United States Patent
Borovetz et al.

[19]

[11] Patent Number: 6,106,776
[45] Date of Patent: Aug. 22, 2000

[54] MEMBRANE APPARATUS WITH ENHANCED MASS TRANSFER VIA ACTIVE MIXING

[75] Inventors: Harvey S. Borovetz; Philip Litwak, both of Pittsburgh; Mark Gartner, McKees Rocks, all of Pa.; Gary D. Reeder, Beulah, Colo.; Patricia Sawzik, Pittsburgh, Pa.

[73] Assignee: University of Pittsburgh, Pittsburgh, Pa.

[21] Appl. No.: 08/837,048

[22] Filed: Apr. 11, 1997

[51] Int. Cl.⁷ ................................................. A61M 1/14
[52] U.S. Cl. .............................................................. 422/44
[58] Field of Search ...................................... 422/44

[56] References Cited

U.S. PATENT DOCUMENTS

| | | |
|---|---|---|
| 3,026,871 | 3/1962 | Thomas . |
| 3,291,568 | 12/1966 | Sautter . |
| 3,332,746 | 7/1967 | Claff et al. . |
| 3,352,422 | 11/1967 | Heden ................................ 210/321.67 |
| 3,396,849 | 8/1968 | Lande et al. . |
| 3,480,401 | 11/1969 | Holm et al. . |
| 3,579,810 | 5/1971 | Mon . |
| 3,674,440 | 7/1972 | Kitrilakis . |
| 3,794,468 | 2/1974 | Leonard . |
| 3,841,837 | 10/1974 | Kitrilakis et al. . |
| 3,907,504 | 9/1975 | Hammond et al. . |
| 3,927,980 | 12/1975 | Leonard . |
| 3,998,593 | 12/1976 | Yoshida et al. . |
| 4,033,724 | 7/1977 | Tamiya ............................ 23/258.5 BH |
| 4,151,088 | 4/1979 | Wolf, Jr. et al. . |
| 4,158,693 | 6/1979 | Reed et al. . |
| 4,163,721 | 8/1979 | Lobdell . |
| 4,165,287 | 8/1979 | Goyne . |
| 4,179,364 | 12/1979 | Bratten et al. . |
| 4,212,741 | 7/1980 | Brumfield . |
| 4,239,625 | 12/1980 | Hlavinka . |
| 4,312,757 | 1/1982 | Brumfield ...................... 210/321.63 X |
| 4,402,420 | 9/1983 | Chernack ................................ 220/266 |
| 4,424,190 | 1/1984 | Mather, III et al. . |
| 4,455,230 | 6/1984 | Elgas et al. . |
| 4,476,685 | 10/1984 | Aid ................................................. 62/3 |
| 4,487,558 | 12/1984 | Troutner .................................. 417/477 |
| 4,490,331 | 12/1984 | Steg, Jr. . |
| 4,573,884 | 3/1986 | Troutner .................................. 417/374 |
| 4,574,876 | 3/1986 | Aid ............................................. 165/46 |
| 4,620,965 | 11/1986 | Fukusawa et al. . |

(List continued on next page.)

FOREIGN PATENT DOCUMENTS

| | | |
|---|---|---|
| 0 140 315 | 5/1985 | European Pat. Off. . |
| 0 331 557 A1 | 9/1989 | European Pat. Off. ........ G01P 15/10 |
| 1437493 | 5/1976 | United Kingdom . |
| WO 90 10237 | 9/1990 | WIPO ............................. G01P 15/10 |
| WO 94/03266 | 2/1994 | WIPO . |

OTHER PUBLICATIONS

"A Dynamic Intravascular Artificial Lung" by Makarewicz et al., ASAIO Journal, 1994, pp. M747–M750.

"A Pumping Artificial Lung" by Makarewicz et al., ASAIO Journal, 1994, pp. M518–M521.

"The Oxygenator" by Yukihiko Nose, Manual on Artificial Organs, 1973, pp. 2–185.

*Lawyers' Medical Cyclopedia*, "I. The Thorax and Respiratory System", §33.1–§33.10, 4–15.

"Resonance Engergies –Respiration, Respiratory System", 215–226.

(List continued on next page.)

*Primary Examiner*—Corrine McDermott
*Assistant Examiner*—Cheryl L. Huseman
*Attorney, Agent, or Firm*—Woodcock Washburn Kurtz Mackiewicz & Norris LLP

[57] ABSTRACT

A blood membrane oxygenator has a housing defining a blood flow path, a rotor hub in the form of a double lumen shaft, and a plurality of distributor disks each having a plurality of hollow fibers which extend across the housing blood flow path. The plurality of distributor disks rotate within the housing to mix the blood resulting in three-dimensional mixing, disruption of the blood boundary layer and efficient blood oxygenation.

12 Claims, 12 Drawing Sheets

U.S. PATENT DOCUMENTS

| | | |
|---|---|---|
| 4,639,353 | 1/1987 | Takemura et al. . |
| 4,659,549 | 4/1987 | Hamada et al. . |
| 4,698,207 | 10/1987 | Bringham et al. . |
| 4,766,768 | 8/1988 | Norling ................................. 73/497 |
| 4,818,490 | 4/1989 | Carson et al. . |
| 4,911,846 | 3/1990 | Akasu et al. ........................ 210/645 |
| 5,002,890 | 3/1991 | Morrison ............................. 435/286 |
| 5,011,469 | 4/1991 | Buckberg et al. ...................... 604/4 |
| 5,034,135 | 7/1991 | Fischel ................................. 210/651 |
| 5,037,383 | 8/1991 | Vaslef et al. . |
| 5,143,630 | 9/1992 | Rolchigo ............................. 210/780 |
| 5,236,665 | 8/1993 | Mathewson et al. ................. 422/46 |
| 5,263,924 | 11/1993 | Mathewson ............................. 604/4 |
| 5,270,005 | 12/1993 | Raible .................................... 422/46 |
| 5,271,743 | 12/1993 | Hattler .................................. 604/26 |
| 5,311,932 | 5/1994 | Sen et al. .......................... 165/109.1 |
| 5,312,589 | 5/1994 | Reeder et al. . |
| 5,626,819 | 5/1997 | Novello et al. ........................ 422/45 |
| 5,668,329 | 9/1997 | Petri ................................. 73/862.59 |
| 5,830,370 | 11/1998 | Maloney, Jr. et al. ............... 210/780 |

OTHER PUBLICATIONS

Extracorporeal Medical Specialties, Inc. (EMSI), Interpulse™ Membrane Oxygenation System, Instructions for Use, 1981, 1–18 (plus 2 sheets of drawing).

Searle Cardio–Pulmonary Systems, Inc., "Searle Membrane Oxygenator" brochure, 1975, 4 pages.

Thomas, J.A. et al., "A Heart–Lung Machine with Artificial Pulmonary Membrane: First Surgical Results", *Arch Mal Coeur*, 1958, 51, 801–811 (English translation included).

Levich, "Diffusion Rates in Turbulent Flow", Ch. III, 139–184 and "Heat Transfer in Fluids", Ch. VI, 185–206 in *Physiochemical Hydrodynamics*, Prentice Hall, Englewood Cliffs, N.J., 1962 (English translation from Russian).

Schlichting, "Origin of Turbulence II", Ch. XVII, 489–554, in *Boundary Layer Theory*, McGraw Hill, New York, 1979 (English translation from German).

Sherwood et al., "Rate Equations for Molecular Diffusion", Ch. 3, in *Mass Transfer*, McGraw Hill, New York, 1975, 54–100.

Sarns, Inc. / 3M, brochure entitled "Membrane Oxygenator", 1988, 2 pages.

MEMBRANE APPARATUS WITH ENHANCED MASS TRANSFER VIA ACTIVE MIXING

BACKGROUND OF THE INVENTION

1. Field of the Invention

This invention relates to a mass transfer apparatus which actively mixes a first mass with a second mass wherein the mass transfer apparatus has hollow fiber membranes carrying the first mass which are rotated or agitated within the second mass thus providing three-dimensional mass transfer. More particularly, this invention concerns a blood oxygenator comprising a rotor hub and a plurality of rotor members each having a plurality of hollow fiber membranes wherein the rotor hub supplies the hollow fiber membranes with oxygen and the plurality of rotor members rotate within the venous blood such that the oxygen which diffuses across the hollow fiber membranes is actively mixed with the venous blood flow.

2. Description of Related Art

The use of membrane oxygenators to oxygenate blood is well known in the art. One type of conventional membrane oxygenator employs bundles of hollow fibers retained within a cylindrical housing wherein oxygen is pumped through the hollow fibers in the same direction as the blood. The hollow fibers consist of a microporous membrane which is impermeable to blood and permeable to gas. Gas exchange takes place when venous blood flows through the housing and contacts the hollow fibers. Based on the law of diffusion the oxygen diffuses across the hollow fiber walls and enriches venous blood in contact with these hollow fibers. Examples of this type of membrane oxygenator are described in U.S. Pat. No. 4,620,965 issued to Eukusawa et al. and U.S. Pat. No. 4,698,207 issued to Bringham et al. The disadvantage to this type of membrane oxygenator is that a blood boundary layer is formed around the hollow fibers which retards oxygenation of blood that does not directly contact the hollow fibers.

Another type of conventional membrane oxygenator provides more efficient oxygenation of blood by positioning blood flow substantially perpendicular or at an angle to the hollow fiber membranes carrying the oxygen. Examples of this type of membrane oxygenator are described in U.S. Pat. No. 4,639,353 issued to Takemura et al., U.S. Pat. No. 3,998,593 issued to Yoshida et al. and U.S. Pat. No. 4,490,331 issued to Steg, Jr. A drawback to these designs is that the permeability of the hollow fiber membranes decreases over time and the oxygenator becomes less efficient.

Yet another type of membrane oxygenator discloses moving a part of the oxygenator in order to provide increased mixing of blood flow. Examples of this type of membrane oxygenator are described in U.S. Pat. Nos. 3,674,440 and 3,841,837 issued to Kitrilakis and Kitrilakis et al., respectively, (the Kitrilakis Patents) and U.S. Pat. No. 3,026,871 issued to Thomas (the Thomas Patent). The Kitrilakis Pats disclose a blood flow path and an oxygen flow path positioned between a rotor and a stator and separated by a membrane and a wafer. When the rotor rotates relative to the stator, mixing of blood flow occurs resulting in disruption of the blood boundary layer. Although this type of oxygenator provides a degree of mixing of blood, this type of mixing results in destruction of the red blood cells.

The Thomas Patent discloses rotating a cylindrical, semipermeable membrane containing oxygen in a housing wherein blood contacts and flows over the membrane and oxygen is transferred through the rotating membrane to the blood. One disadvantage of this type of membrane oxygenator is that the permeability to oxygen and carbon dioxide of semipermeable membranes is poor.

Yet another type of blood oxygenator device comprises short microporous fiber sheets which are folded, twisted and woven around a hollow shaft that carries the inlet and outlet gas flows. The device is implanted into the vascular system of a patient and rotated to cause mixing of the blood. This type of device is explained in greater detail in "A Dynamic Intravascular Lung," ASAIO Journal 1994. The problem with this type of blood oxygenator is that the number of fiber sheets that are able to be incorporated into the device is limited because the device is an intravascular device and therefore, anatomical space is limited. Furthermore, the rotation of the device within the blood vessel may destroy the cells lining the blood vessel.

Nowhere in the cited related art is there disclosed or suggested a membrane oxygenator which provides effective blood oxygenation to sustain a patient for extended durations while also providing a compact oxygenator design. Therefore, there is a definite need for a blood membrane oxygenator incorporating an active mixing component which provides for effective blood oxygenation.

SUMMARY OF THE INVENTION

Accordingly, the present invention provides a blood oxygenator having a housing defining a blood path, a rotor hub defining an oxygen path, and at least one rotor defining a blood path and having a plurality of hollow fibers extending across the rotor blood path and being in fluid communication with the rotor hub oxygen path such that when oxygen flows through and diffuses across the plurality of hollow fibers and the rotor rotates about the rotor hub, active mixing of the blood occurs resulting in disruption of the blood boundary layer surrounding the hollow fibers.

Preferably, the rotor is a distributor disk having two oxygen return channels, two oxygen supply channels, a first spoke defining an oxygen inlet path, a second spoke defining an oxygen outlet path and a plurality of hollow fibers extending across the diameter of the disk and in fluid communication with the return and supply channels.

The present invention preferably provides a plurality of distributor disks positioned on the rotor hub thus, providing additional hollow fibers and increased surface area of the hollow fibers at which oxygenation of the blood takes place. The specific number of distributor disks is dependent upon the amount of surface area necessary for the specific patient. For example, a larger patient requires greater oxygen delivery and thus, more disks, however, fewer disks are necessary for a smaller patient. Further, the present invention provides for the surface area of the hollow fibers to be increased by increasing the number of hollow fibers on each distributor disk. Hollow fibers can extend from both the first and second faces of each of the distributor disk. By increasing or decreasing the number of distributor disks and hollow fibers used in the blood oxygenator of the present invention, the blood oxygenator capacity can be tailored to the specific patient application.

The present invention further provides for each of the plurality of rotors to be able to rotate independently of one another such that while some rotors rotate in the clockwise direction the other rotors simultaneously rotate in the counter-clockwise direction thus, providing an enhanced mixing of blood. Also, the plurality of rotors can be rotated in a back and forth motion such that the rotors repeatedly rotate approximately 360 degrees or less, and then reverse direction resulting in the blood being agitated and the blood boundary layer being disrupted.

Baffles are preferably positioned between the plurality of rotors in the blood oxygenator of the present invention in order to provide an increased mixing of the blood.

The rotor hub preferably takes the form of a double lumen shaft defining an oxygen inlet path and an oxygen outlet path.

The present invention provides for the plurality of hollow fibers to be microporous such that the fibers are impermeable to liquid and are permeable to gas. The present invention further provides for the opportunity of the surfaces of the hollow fibers to be coated with a material which would decrease the wetability of the microporous structure. An example of the type of material used for these purposes is silicone rubber, although numerous other polymer coatings could be used.

The present invention provides a blood oxygenator that can be used to treat patients having acute as well as chronic lung diseases.

Other details, objects and advantages of the present preferred invention will become more apparent with the following description of the present preferred invention.

BRIEF DESCRIPTION OF THE DRAWINGS

The accompanying drawings describe the present preferred invention in which.

DETAILED DESCRIPTION OF THE PRESENT PREFERRED INVENTION

Although this invention is suitable for other uses it will be described as being used as a blood oxygenator to support a patient. Such description is for purposes of explanation and is not intended to limit the scope of this invention. For example, the present invention can be used as a kidney dialysis machine.

FIGS. 1–5 illustrate a present preferred embodiment of a blood oxygenator 10 comprising a housing 12 defining a blood flow path 13, a rotor hub in the form of a double lumen shaft 14, and a plurality of rotors each comprising a hollow fiber distributor disks 16. The housing 12 encases the rotor hub 14 and the hollow fiber distributor disks 16. The housing has a venous blood inlet 18, an arterial blood outlet 20, an oxygen supply inlet 22 and a gas outlet 24 and is preferably made from polycarbonate. Within the housing 12 is an inlet chamber 25 and an outlet chamber 27. The double lumen shaft defines an oxygen inlet path 29 and a gas outlet path 31. The oxygen inlet path 29 is in fluid communication with the oxygen supply inlet 22 and the gas outlet path 31 is in fluid communication with gas outlet 24.

Referring to FIGS. 5–13, each of the plurality of hollow fiber distributor disks 16 is fixedly mounted on the double lumen shaft 14. Each of the hollow fiber distributor disks 16 comprises (FIG. 11) an interior surface 28, an exterior surface 30 concentric to the interior surface 28, a first face 32, a second face 34, a first spoke 36 and a second spoke 38 and a plurality of hollow fibers 48. The first face 32 and the second face 34 each have an arcuate-shaped supply channel 40 and an arcuate-shaped return channel 42. The supply channels 40 and the return channels 42 are spaced apart a defined length 44. The first spoke 36 defines an oxygen supply path and is connected at its distal end 39 to the distributor disk 16 and is connected at the proximal end 41 to the oxygen inlet path 29 of the double lumen shaft 14. The second spoke 38 defines a gas return path and is connected at its distal end 47 to the distributor disk 16 and is connected at the proximal end 46 to the gas outlet path 31 of the double lumen shaft 14. Each of the first and second spokes 36, 38 act as a support for the distributor disk 16.

A plurality of microporous hollow fibers 48 extend across the diameter of the distributor disk 16 and weave around the double lumen shaft 14. The hollow fibers 48 extend across the first face 32 and the second face 34 of the distributor disk 16. The plurality of hollow fibers 48 are connected to the supply and return channels 40, 42 of the distributor disks 16 by potting material 49 which can be an epoxy resin. A Y-shaped return tunnel 50 and a Y-shaped supply tunnel 52 shown in greater detail in FIGS. 10 and 11 connect the supply and return channels 40, 42 with the first and second spokes 36 and 38, respectively.

The hollow fibers 48 are made from a microporous material which is permeable to gases and impermeable to liquids. However, if the present invention is used in a kidney dialysis machine the material of the hollow fibers 48 would have to be permeable to fluid. For oxygenation, the preferred material is polypropylene; however, other materials depending upon the application such as polyethylene can be used to form the hollow fibers 48.

Figure 1:
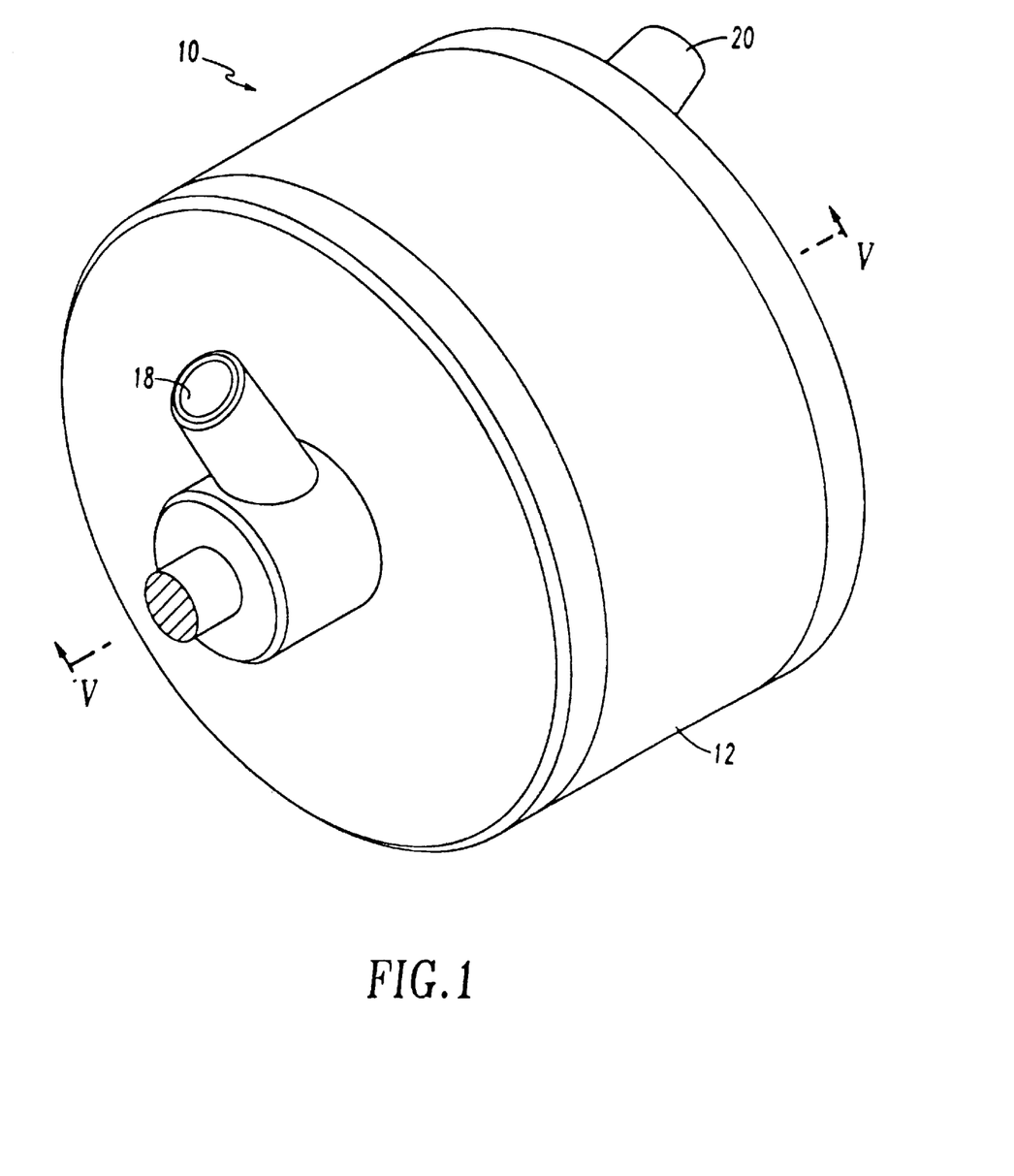
FIG. 1 is a perspective view of the preferred embodiment of the present invention blood membrane oxygenator illustrating the venous blood inlet and arterial blood outlet.
Figure 2:
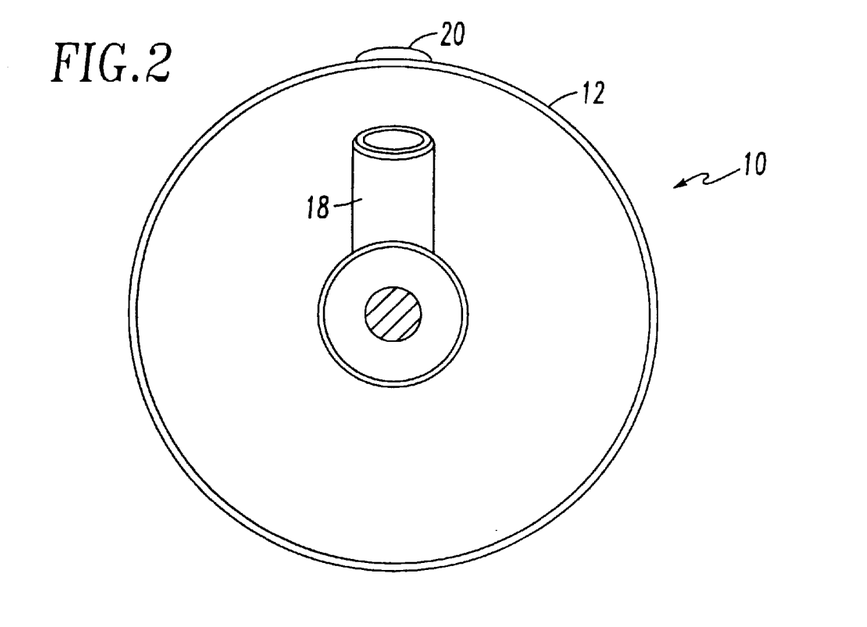
FIG. 2 is a front plan view of the blood oxygenator shown in FIG. 1 illustrating the venous blood inlet.
Figure 3:
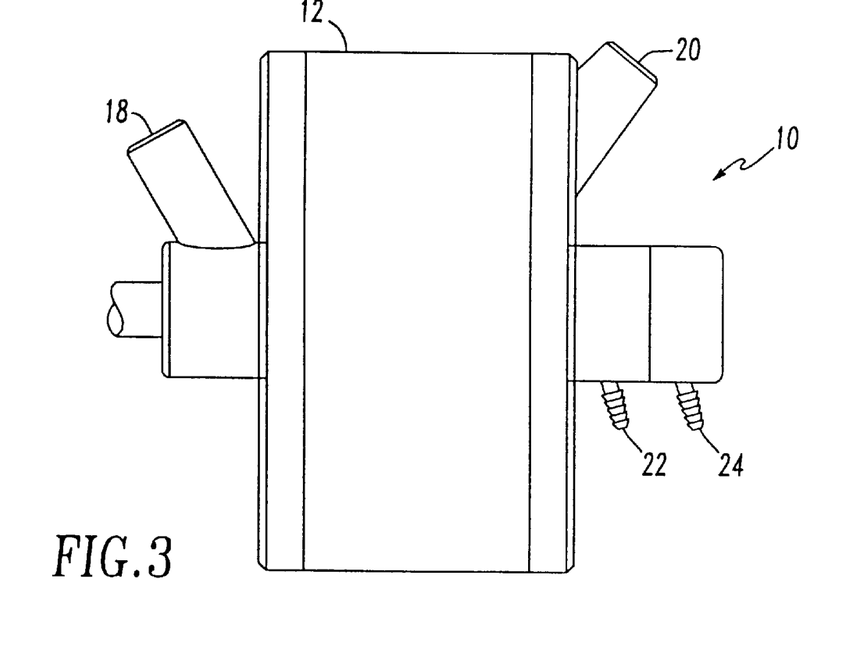
FIG. 3 is a side plan view of the blood oxygenator shown in FIG. 1 further illustrating an oxygen inlet and an oxygen outlet.
Figure 4:
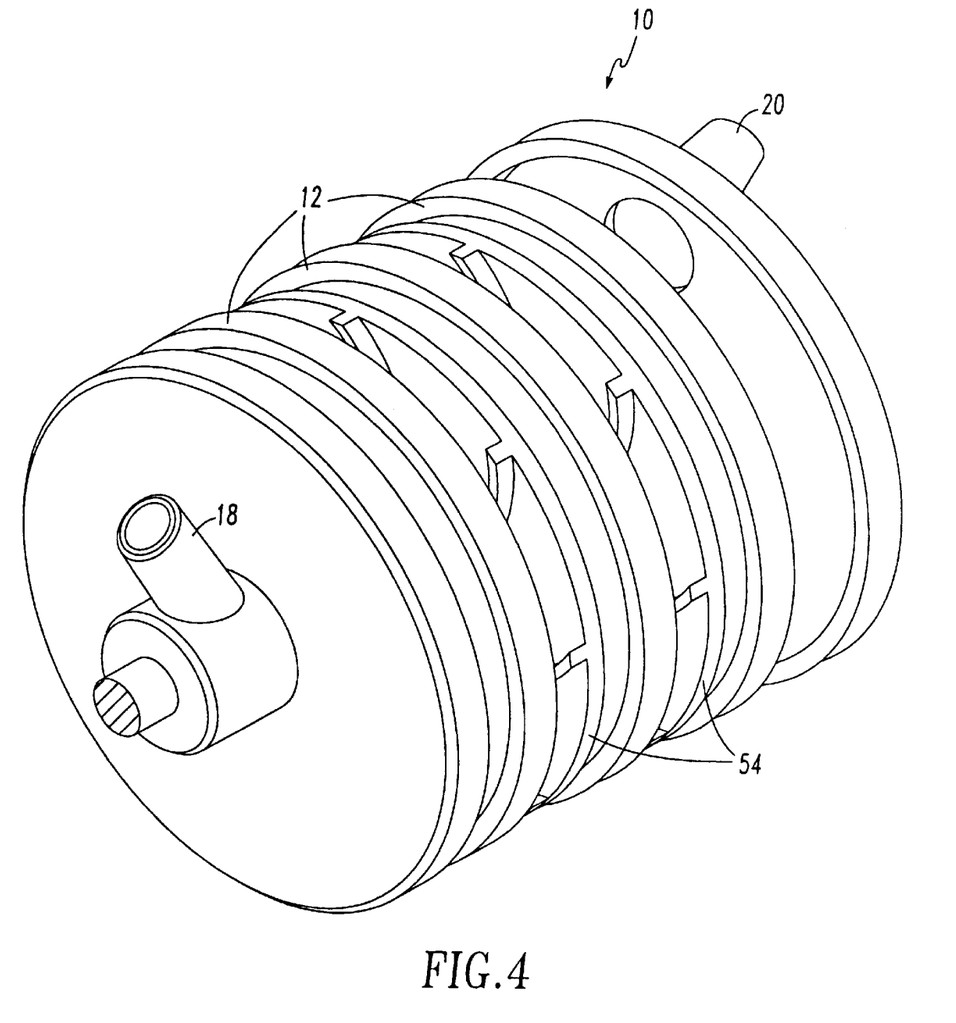
FIG. 4 is a cutaway perspective view of the blood oxygenator shown in FIG. 1 with some of the cylindrical section of the housing and the rotors eliminated in order to more clearly illustrate one embodiment of the baffles.
Figure 5A:
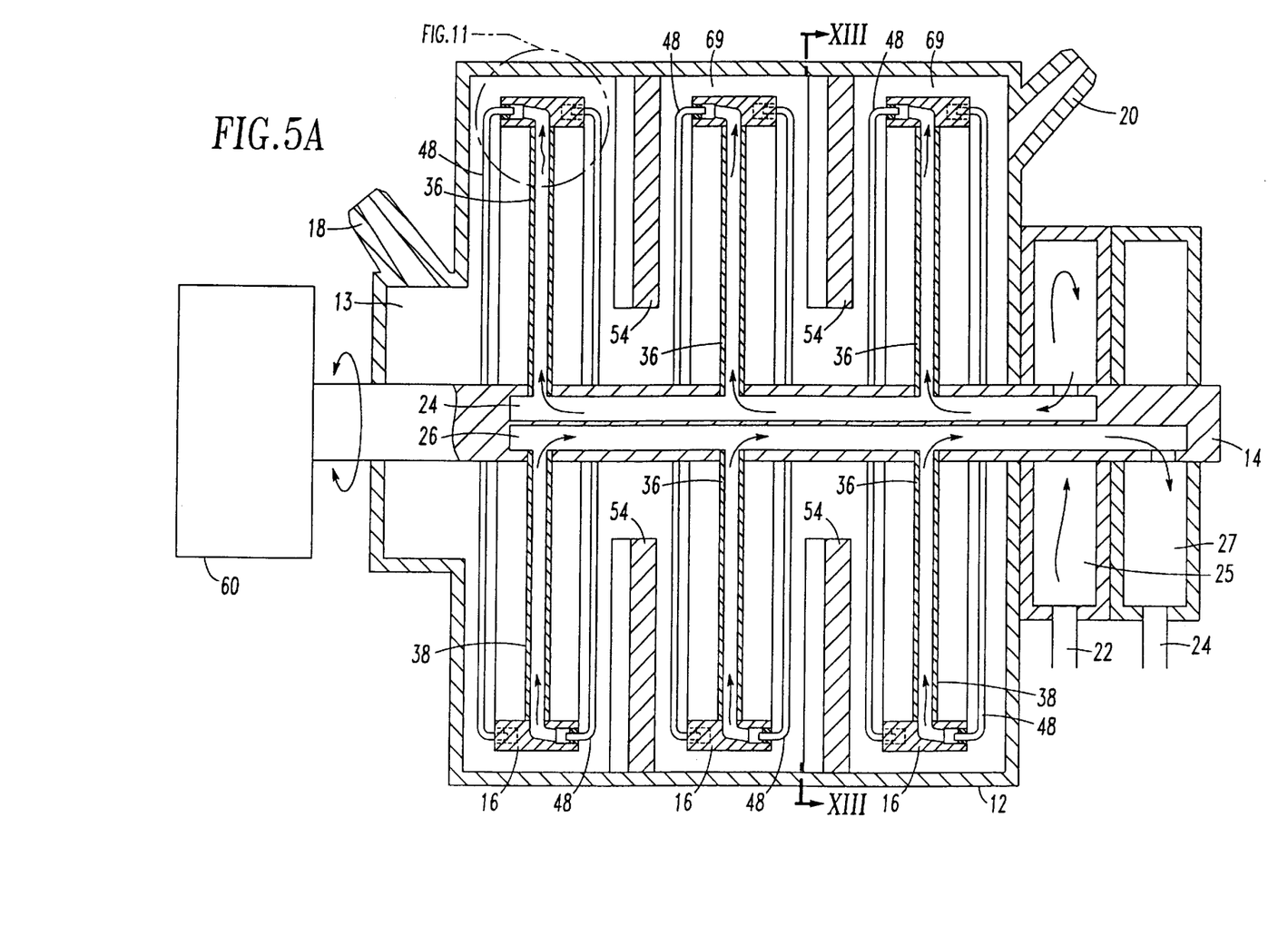
FIG. 5a is a cross-sectional view of the blood oxygenator shown in FIG. 1 taken along line V—V and illustrating the gas flow path.
Figure 5B:
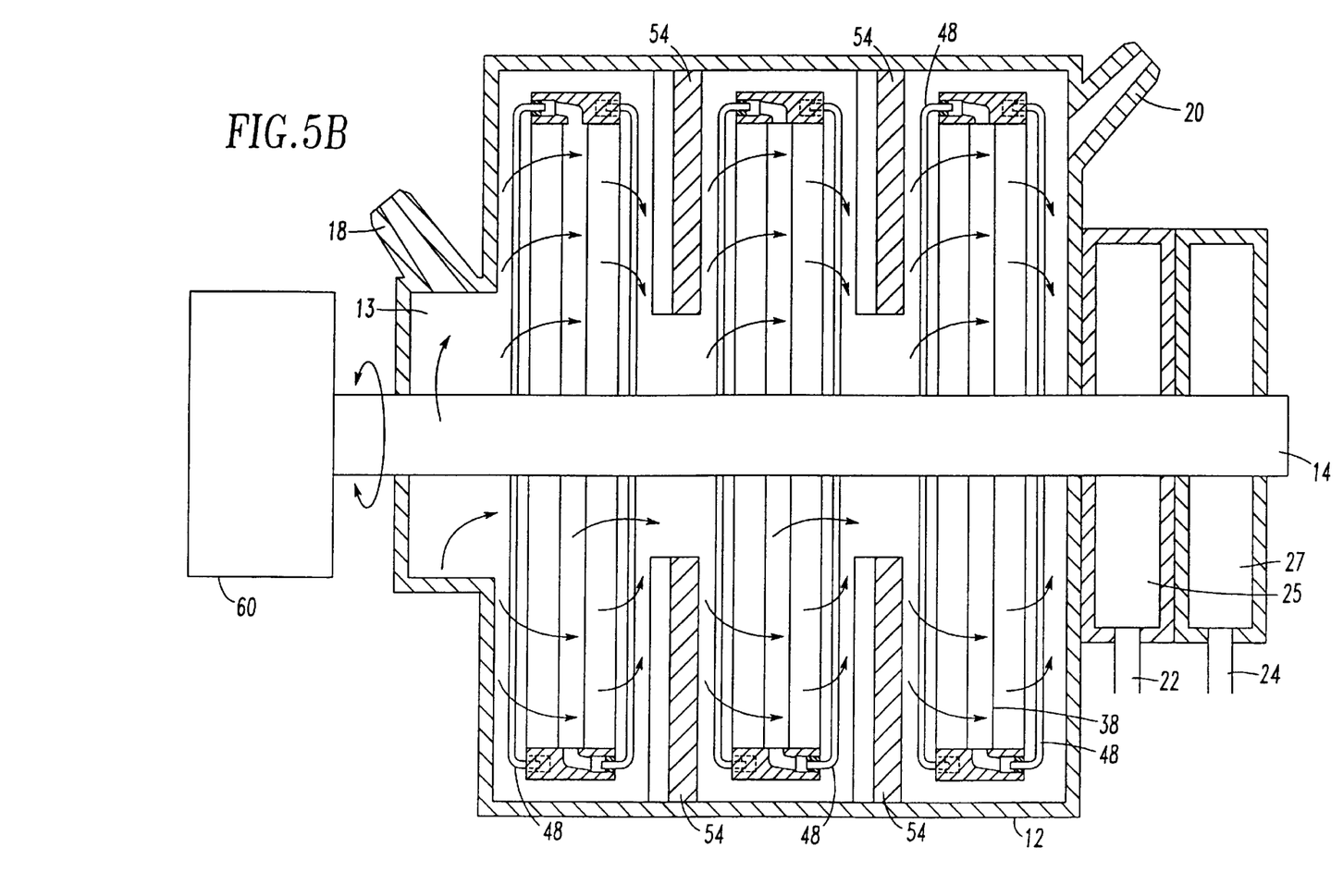
FIG. 5b is the cross-sectional view of the blood oxygenator shown in FIG. 1 taken along line V—V and illustrating the blood flow path.
Figure 6:
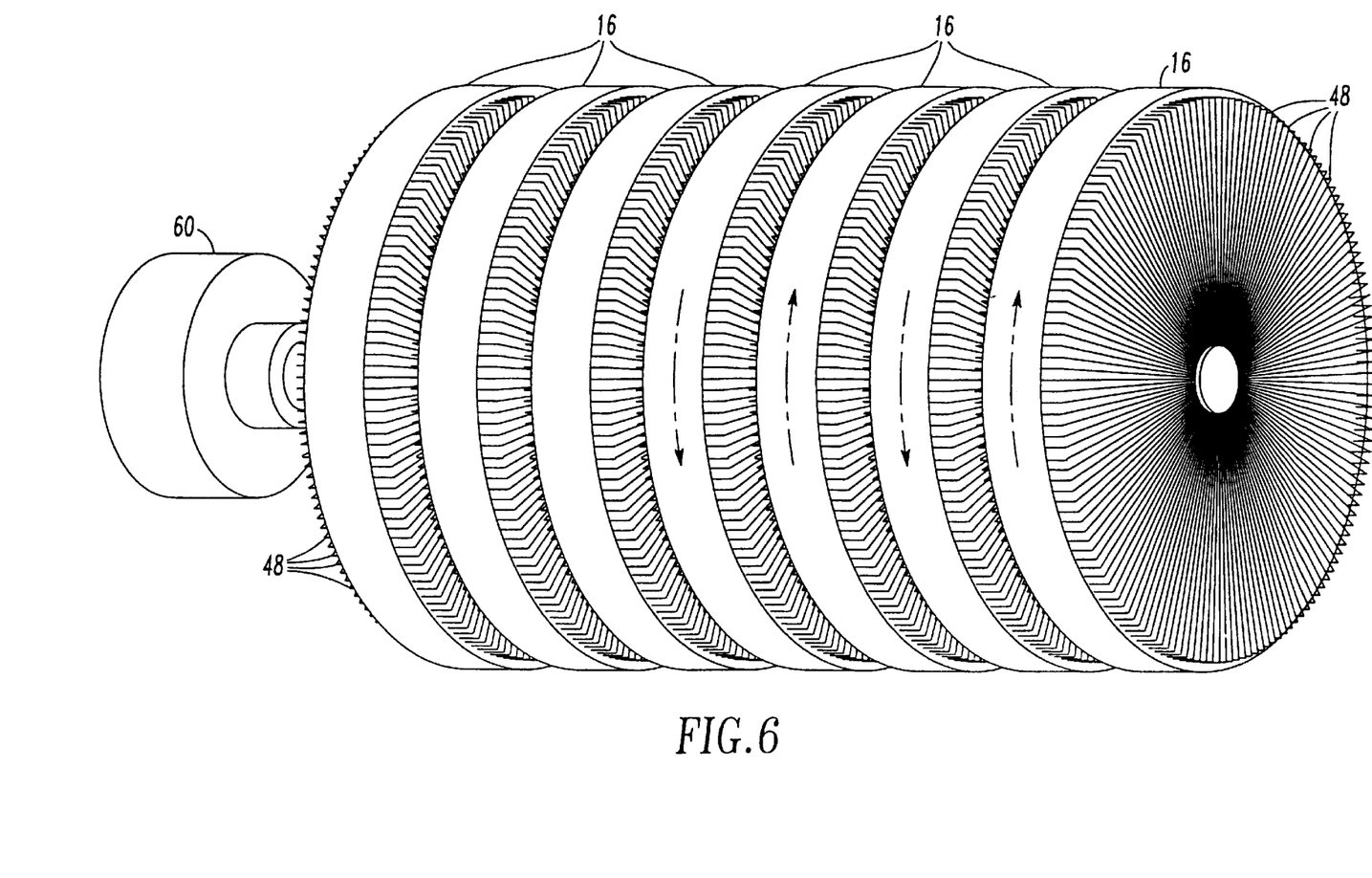
FIG. 6 is a perspective view of a plurality of hollow fiber distributor disks mounted on a double lumen shaft of the present preferred invention.
Figure 7:
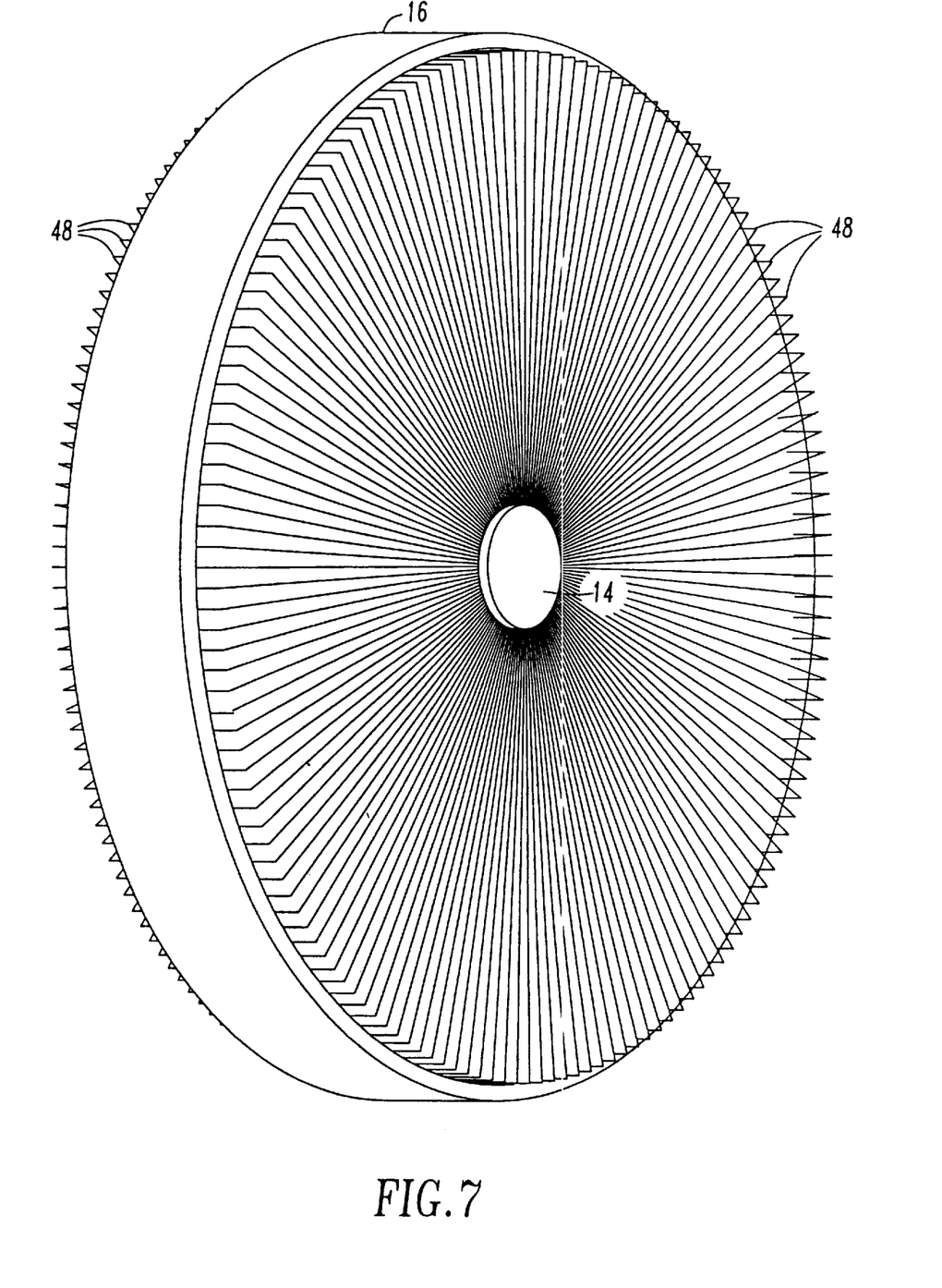
FIG. 7 is a perspective view of one of the hollow fiber distributor disks shown in FIG. 6.
Figure 8:
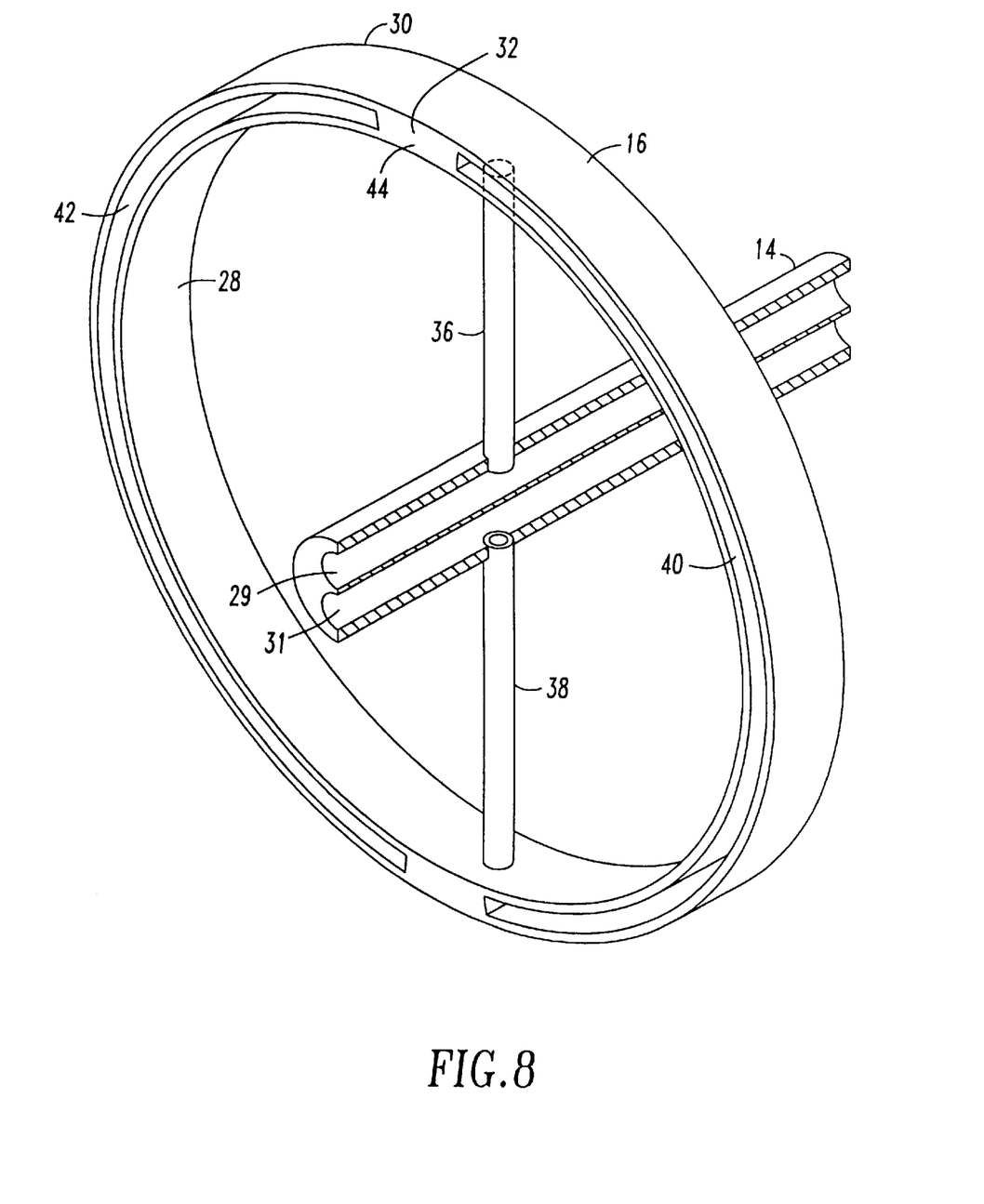
FIG. 8 is a perspective view of one of the hollow fiber distributor disks shown in FIG. 6 with the hollow fiber members eliminated therefrom.
Figure 9:
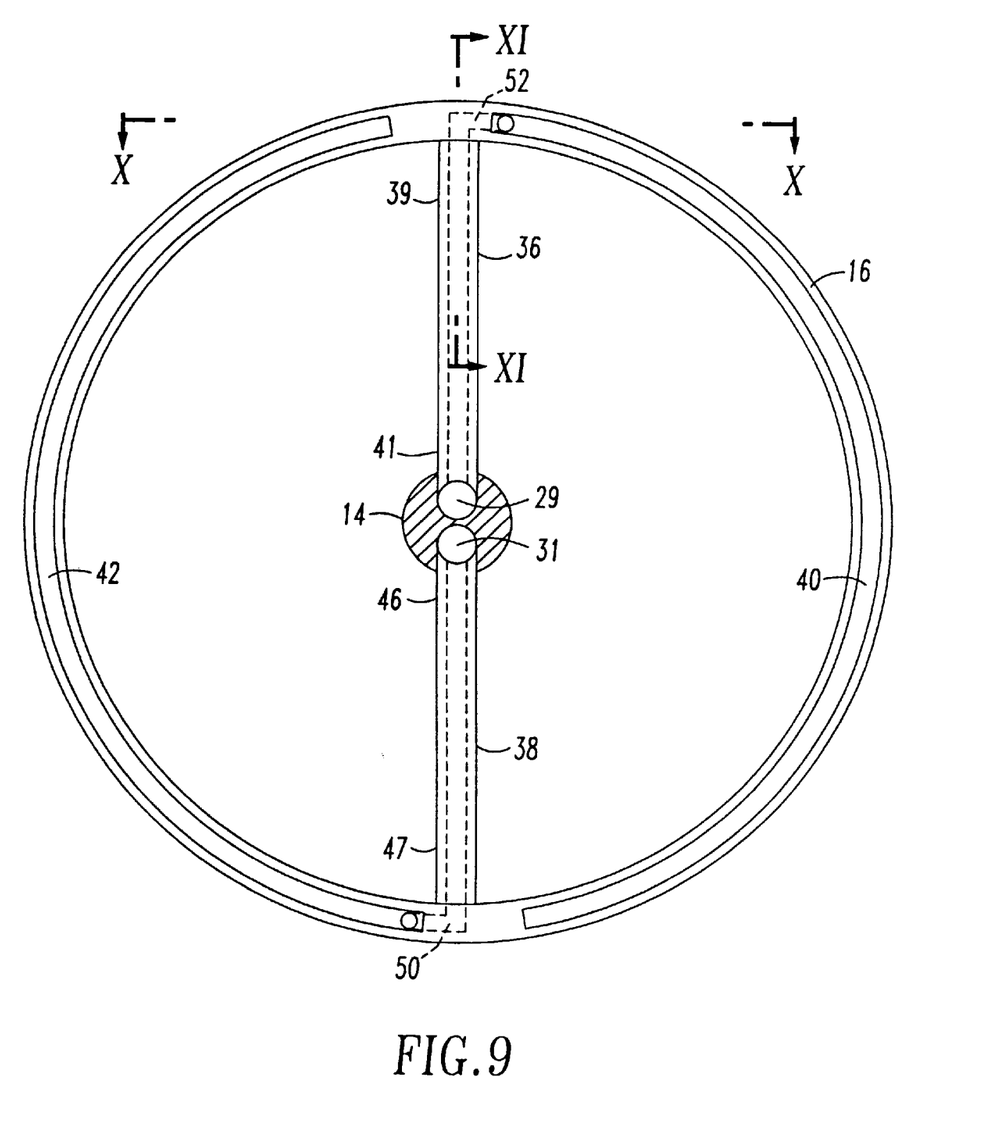
FIG. 9 is a side plan view of the hollow fiber distributor disk shown in FIG. 8.
Figure 10:
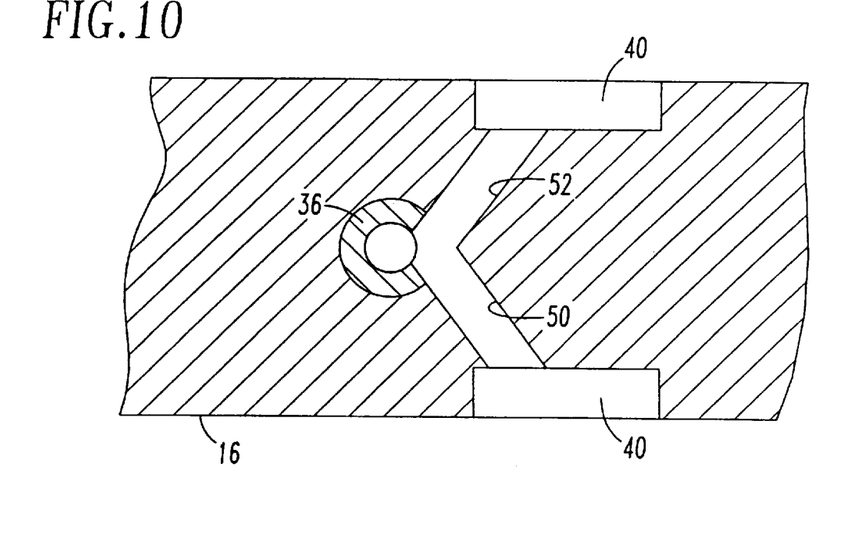
FIG. 10 is a cross-sectional view of the hollow fiber distributor disk shown in FIG. 9 taken along line X—X.
Figure 11:
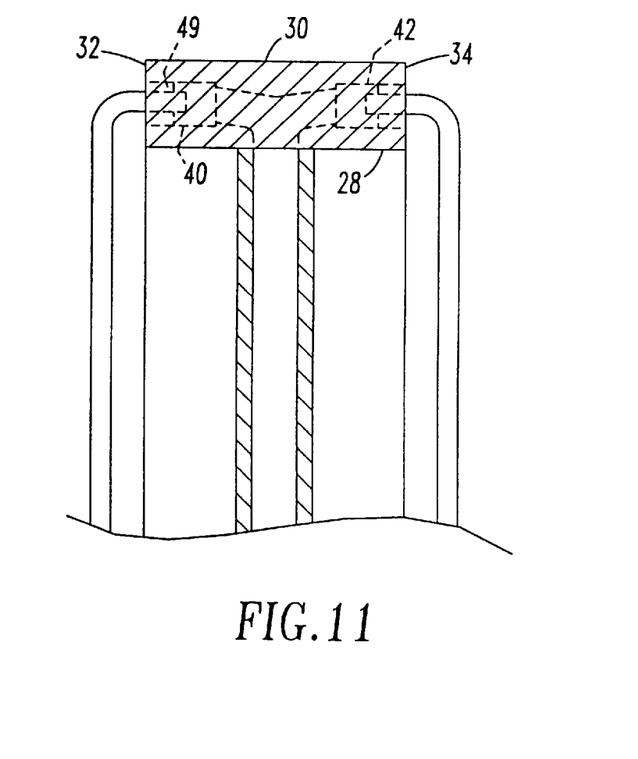
FIG. 11 is an enlarged view of a hollow fiber distributor disk shown in FIG. 5a illustrating the fluid connection of the hollow fibers with the channels of the distributor disk.
Figure 12:
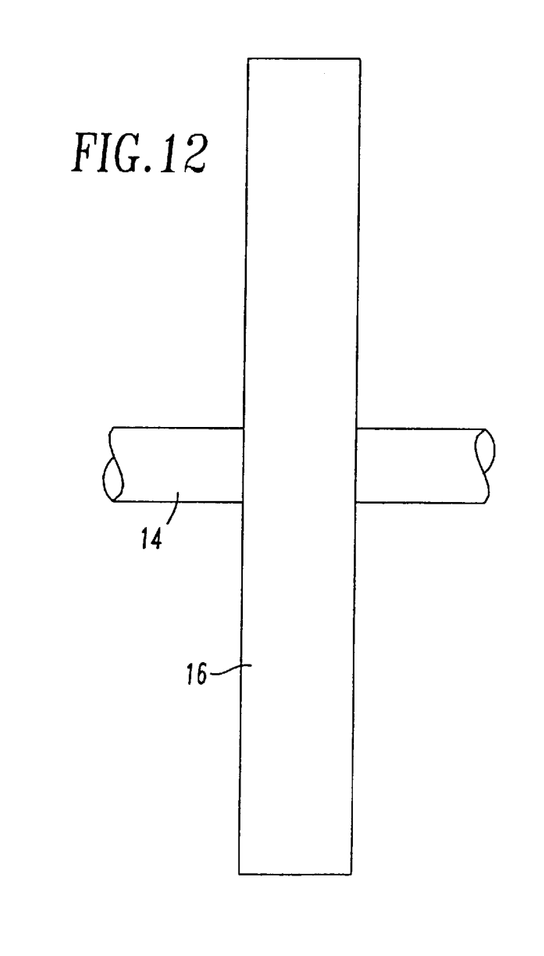
FIG. 12 is a side plan view of the hollow fiber distributor disk shown in FIG. 8.
Figure 13:
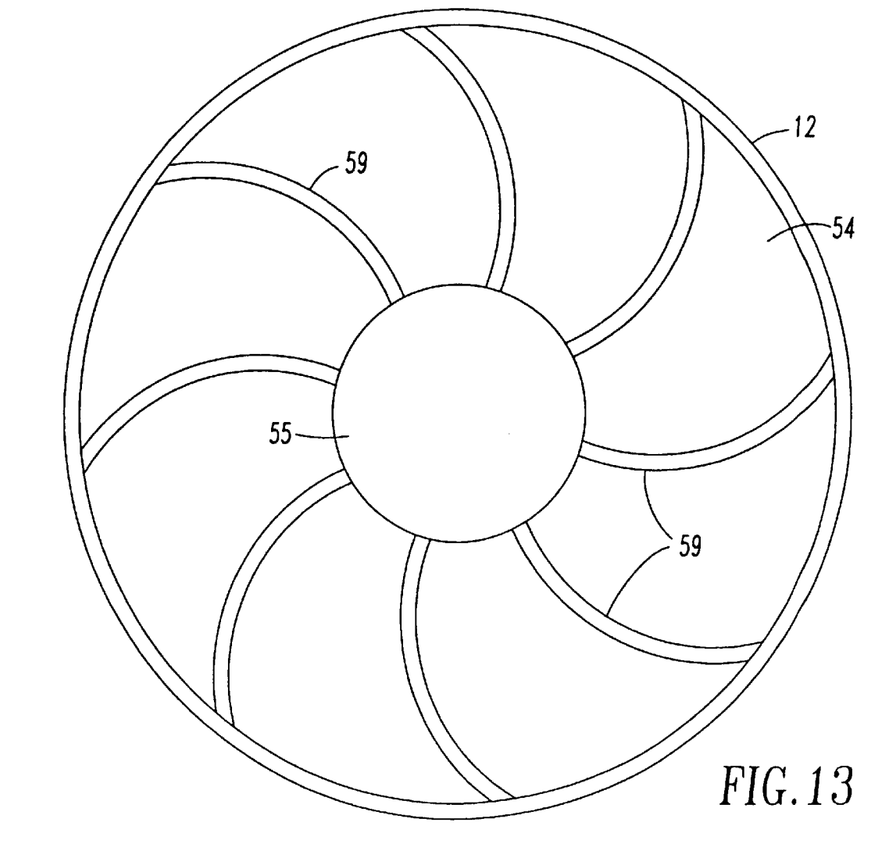
FIG. 13 is a cross-sectional view of the blood oxygenator shown in FIG. 5 taken along line XIII—XIII which illustrates the baffles.

Sets of baffles 54, shown in greater detail in FIGS. 5 and 13, are interspersed between the distributor disks 16. The baffles 54 are integral disks extending from the inner wall of the device housing 12 toward the center of the blood flow path, thereby defining a partition 69 within the housing 12 in which a distributor disk 16 will rotate. Each baffle 54 defines a central opening 55 of sufficient diameter to allow flow from one segment of the housing 12 to the next. Additionally, the surfaces of each baffle 54 will have an elevated rib or flute 59 which will serve to provide direction to blood flowing off the surface of the rotating distributing disks 16. The baffle cross section can take many other shapes.

The distributor disks 16 rotate about the axis of the double lumen shaft 14. The distributor disks 16 can either rotate in one direction or in a back and forth motion. When rotating in one direction all of the distributor disks rotate in either clockwise or counter-clockwise direction. When the distributor disks 16 are rotating in a back and forth manner each of the distributor disks 16 rotate in one direction for a specified angle and then change directions and rotate in the opposite direction for a specified angle. This back and forth motion agitates the blood surrounding the hollow fibers 48 thus, disrupting the blood boundary layer. The distributor disks 16 are actuated using a conventional electric motor 60. However, other motor technologies can be used.

Referring to FIGS. 5a and 5b, the present preferred embodiment provides for the following blood flow paths and oxygen flow paths. Oxygen enters through the oxygen supply inlet 22, proceeds through the inlet chamber 25, and flows through the oxygen inlet path 29 of the double lumen shaft 14. The oxygen is then transported into the plurality of first spokes 36 which are in fluid communication with the double lumen shaft inlet path 29 at the first spokes proximal end 41 and in fluid communication with the Y-shaped supply tunnels 52 at its distal end 39. The oxygen then passes through the tunnels 52 and supply channels 40 and enters the hollow fibers 48, flows through the hollow fibers 48 extending across the diameter of the distributor disks 16 where the oxygen exchange takes place. In accordance with the law of diffusion, oxygen travels across the walls of the microporous hollow fibers 48 into the venous blood while simultaneously carbon dioxide contained within the venous blood travels across the walls of the hollow fibers 48 into the return gas flow path. The oxygen/carbon dioxide mixture within the hollow fibers 48 enters the return channels 42 of the distributor disks 16 and is transmitted through the Y-shaped return tunnels 50 to the second spoke 38 and then to the gas outlet path 31 of the double lumen shaft 14.

Referring to FIG. 5b, venous blood enters the blood inlet 18, flows through the cylindrical portion 13 of the housing 12 where the venous blood contacts the hollow fibers 48 of the rotating distributor disks 16. The venous blood flow path is substantially perpendicular to the hollow fibers 48 and provides for a degree of mixing and cross-flow of blood which results in a disruption of the blood boundary layer. Further, the rotation of the hollow fibers 48 on each of the distributor disks 16 and the presence of the baffles 54 between the rotating distributor disks 16 provides for a greater degree of mixing of blood resulting in enhanced oxygenation. The venous blood directly contacts and surrounds the walls of the hollow fibers 48 providing three-dimensional oxygenation. The oxygen-enriched blood then exits through the arterial blood outlet 20. By rotating the distributor disks 16 which carry the hollow fibers 48 through the venous blood, three dimensional mixing and efficient oxygenation are realized.

Figure 14:
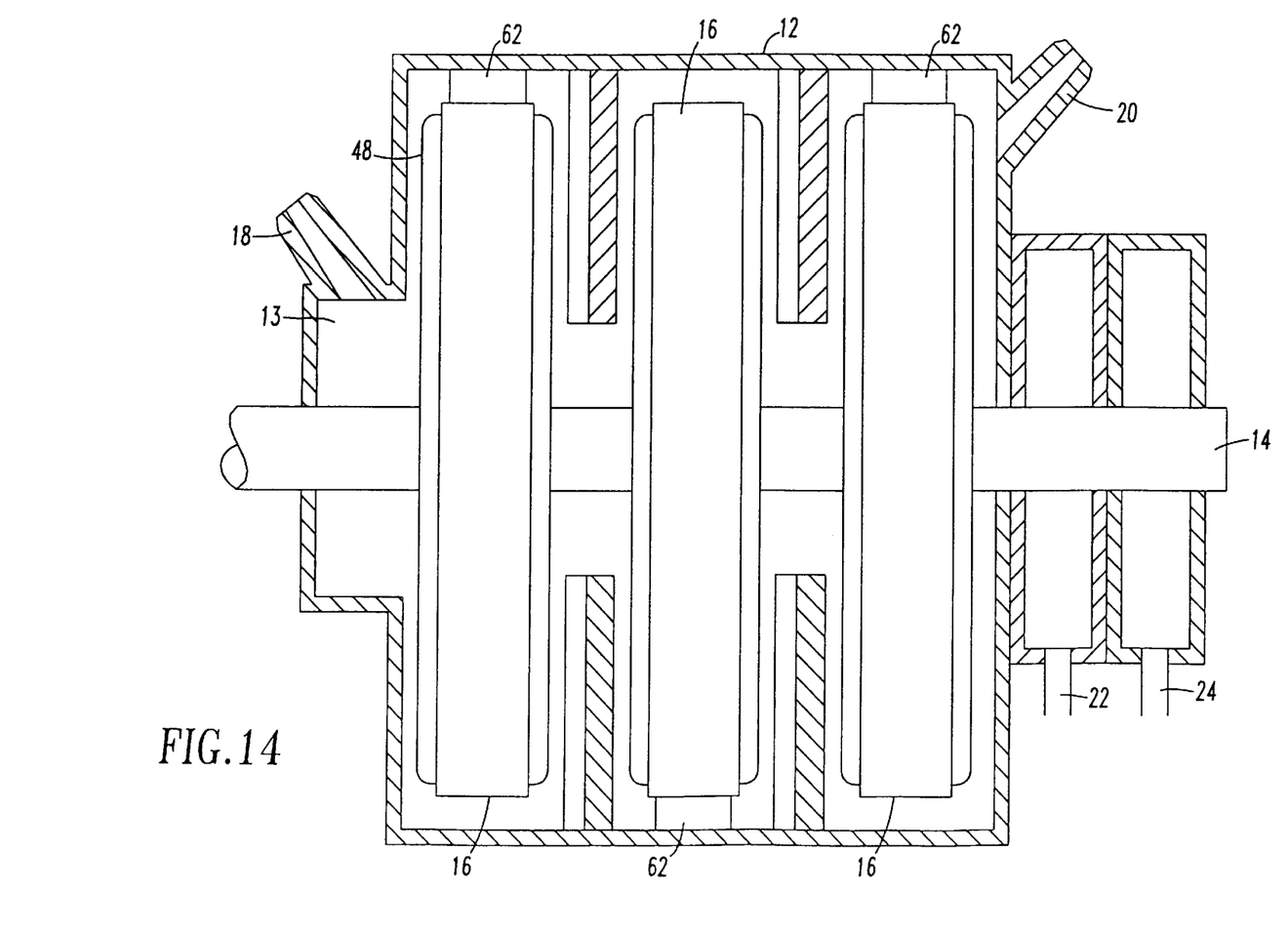
FIG. 14 is a cross-sectional view of a blood oxygenator similar to the blood oxygenator shown in FIG. 5a which employs a series of drive rollers to impart the rotational movement to the distributor disks.

Referring to FIG. 14, alternating counter-rotation of the distributor disks 16 can be achieved by a series of drive rollers 62, rotating in opposite directions, which firmly contact the outer edge of the distributor disks 16 thereby imparting rotational movement to the distributor disk 16. When rotating in the alternating counter-rotation manner some of the distributor disks 16 rotate clockwise while the other distributor disks 16 simultaneously rotate counter-clockwise. This alternating counter-rotation provides for disruption of the boundary layer of blood contacting the hollow fibers 48 resulting in increased oxygenation. Alternatively, the disks 16 could be mounted on coaxial shafts which are turned in opposite directions to impart counter-rotation of the alternating distributor disks 16.

While the present invention has been described herein, it is distinctly understood that the invention is not limited thereto but may be otherwise variously embodied in the scope of the following claims and any equivalent thereof.

We claim:

1. A mass transfer apparatus comprising:
   (a) a housing defining a first fluid path and having a first fluid inlet, a first fluid outlet, a second fluid inlet and a second fluid outlet;
   (b) a rotor hub defining at least one second fluid flow path which is in fluid communication with the second fluid flow inlet and the second fluid flow outlet;
   (c) at least one rotor defining a first fluid flow path and defining at least one second fluid flow path in fluid communication with the rotor hub at least one second fluid flow path; and
   (d) a plurality of hollow fibers each in fluid communication with the at least one rotor second fluid flow path and extending across the housing first fluid flow path such that when a first fluid flows through the housing first fluid flow path and a second fluid flows through and diffuses across the plurality of hollow fibers and the rotor rotates about the rotor hub, a fluid exchange between the first and second fluids occurs through the walls of the plurality of hollow fibers.

2. A gas transfer apparatus comprising:
   (a) a housing defining a fluid flow path and having a fluid inlet, a fluid outlet, a gas inlet and a gas outlet;
   (b) a rotor hub defining at least one gas flow path in fluid communication with the gas inlet and the gas outlet;
   (c) at least one rotor defining a fluid flow path and defining at least one gas flow path wherein the at least one gas flow path is in fluid communication with the rotor hub at least one gas flow path;
   (d) a plurality of hollow fibers, each of the plurality of hollow fibers extending across the at least one rotor fluid flow path and in fluid communication with the at least one gas flow path; and
   wherein when a fluid flows through the housing path and a gas flows through and diffuses across the plurality of hollow fibers and the at least one rotor is rotated about the rotor hub, the fluid will be enriched by the gas as a result of the gas directly contacting and surrounding the plurality of hollow fibers and the mixing of the fluid.

3. The gas transfer apparatus of claim 2 further comprising a means for rotating the at least one rotor.

4. The gas transfer apparatus of claim 2 wherein the disks have channels milled therein and the plurality of hollow fibers extend from the channels of the disks.

5. The gas transfer apparatus of claim 2 wherein the plurality of hollow fibers are made from a microporous material which is substantially impermeable to fluid and permeable to gas.

6. The gas transfer apparatus of claim 2 wherein the hollow shaft is a double lumen shaft defining a gas inlet path and a gas exit path.

7. The gas transfer apparatus of claim 3 wherein the at least one rotor is a plurality of rotors.

8. The gas transfer apparatus of claim 7 wherein the rotating means independently rotate each of the plurality of rotors such that some of the plurality of rotors can rotate clockwise while other of the plurality of rotors can simultaneously rotate counter-clockwise.

9. The gas transfer apparatus of claim 2 wherein the fluid flow path is substantially perpendicular to the plurality of hollow fiber.

10. The gas transfer apparatus of claim 2 further comprising an agitator which rotates the rotor hub and the at least one rotor in a back-and-forth motion.

11. The gas transfer apparatus of claim 2 further comprising a plurality of baffles between the fluid flow inlet and the at least one rotor.

12. The gas transfer apparatus of claim 2 wherein the at least one rotor has a first face and a second face and the plurality of hollow fibers extend from both the first face and the second face.

* * * * *